United States Patent [19]

Bergman et al.

[11] 4,198,434

[45] Apr. 15, 1980

[54] GLUCONYL HYDRAZIDES

[75] Inventors: Janice M. Bergman, Kansas City, Mo.; Kurt J. Bevernitz, Mission; Jerry L. Rutter, Overland Park, both of Kans.

[73] Assignee: Gulf Oil Corporation, Pittsburgh, Pa.

[21] Appl. No.: 14,402

[22] Filed: Feb. 23, 1979

Related U.S. Application Data

[63] Continuation-in-part of Ser. No. 931,236, Aug. 7, 1978, abandoned.

[51] Int. Cl.$^2$ .............................................. A01N 9/20
[52] U.S. Cl. ................................. 424/320; 260/551 R
[58] Field of Search ......................................... 424/320

[56] References Cited

U.S. PATENT DOCUMENTS

| | | | |
|---|---|---|---|
| 2,355,911 | 8/1944 | Graenacher et al. | 536/53 |
| 3,092,660 | 6/1963 | Gutmann et al. | 260/561 H |
| 4,021,542 | 5/1977 | Schmidt et al. | 424/180 |

OTHER PUBLICATIONS

Grinsteins et al, C. A. vol. 68 (1968) 76830v.
Jermyn, Oust. J. Biochem. Sciences 22 (1969) pp. 1039–1049.
Kiliani, C. A. Volzo (1926) 2985–2987.
Van Mar Le, C. A. 15 (1920) p. 364.
Todd et al, C. A. vol. 64 (1966) 9808.
Zbigniew, C. A. vol. 63 (1965) 3024.
Varvawina et al, C. A. vol. 84 (1976) 90488b.
Swiderski et al, C. A. vol. 49 (1953) 1572b.

*Primary Examiner*—Allen J. Robinson
*Attorney, Agent, or Firm*—Donald R. Cassady

[57] ABSTRACT

Southern army worm metamorphosis can be interrupted and certain microorganisms, as for example, bacteria, fungi, molds and algae, can be inhibited by contact with an effective growth-inhibiting concentration of gluconic acid hydrazides of the group consisting of the N-(lower alkyl) gluconyl hydrazides.

1 Claim, No Drawings

GLUCONYL HYDRAZIDES

This application is a continuation-in-part of application Ser. No. 931,236, filed Aug. 7, 1978, now abandoned.

BACKGROUND OF THE INVENTION

Gluconic acid is an oxidation product of the monomeric sugar, glucose. It exists to a large extent as the cyclic lactone in aqueous solution. The aryl hydrazide derivatives of gluconic acid are well known and have been used to study the optical rotation of the sugar acid. The alkyl and cycloalkyl hydrazides are not well known. The β-hydroxyethyl-, isopropyl-, and benzyl hydrazides were reported by V. Grinsteins, et al., Latv. P.S.R. Zinat. Akam. Vestis Kim. Ser. (1967(6), 705–16 (Russ.) to be anti-depressants, and the benzyl- and isopropyl hydrazides were identified by Gutman in U.S. Pat. No. 3,092,660 as monoamine oxidase inhibitors.

Gluconic acid has been disclosed as a buffer in an anti-mocrobial peptone solution by Hecht and Fredenburgh in U.S. Pat. No. 2,732,326.

SUMMARY OF THE INVENTION

Gluconyl hydrazides of the formula

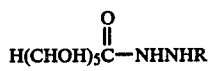

wherein R is lower alkyl are growth inhibitors of many microbes which contaminate common laboratory and household apparatus and supplies as for example, work benches, cabinets, bathroom and other sanitary facilities, "clean" rooms and other similar surfaces. The compounds are active in aqueous solution at effective inhibitory concentrations of, for example, 0.05 to 0.2 M, against surface contamination.

Suprisingly, the compounds also exhibit microbial inhibitory activity against the usual contaminants in aqueous mixtures as for example in dispersions, slurries, suspensions, colloidal solutions, and the like. As for example, to control slimes and bacterial, algal, and fungal contamination in holding tanks, ponds, recirculating systems, cutting oils, and the like.

Further, it has been discovered that the compounds also disrupt the metamorphosis of the southern army worm, and as such can be used as a control for the spread of this insidious pest. The larvae are unable to pupate and will shrivel up and die. In use the compound is incorporated into an infested field with a diluent or emulsifier, dispersant or the like in concentrations of 100 to 500 ppm.

DETAILED DESCRIPTION OF THE INVENTION

The hydrazides of this invention are stable, organic compounds exhibiting activity as microbial growth inhibitors and insecticides. They exhibit their growth inhibitory activity and chemosterilant activity when applied to contaminated surfaces and in aqueous mixtures, in liquid compositions, and dust compositions. The term "lower alkyl" shall include methyl, ethyl, n-propyl, isopropyl, n-butyl, isobutyl, sec-butyl, and tert-butyl. The compounds useful in the method of the invention are:

N-methyl gluconyl hydrazide
N-ethyl gluconyl hydrazide
N-n-propyl gluconyl hydrazide
N-isopropyl gluconyl hydrazide
N-n-butyl glucanyl hydrazide
N-isobutyl gluconyl hydrazide
N-sec-butyl gluconyl hydrazide
N-tert-butyl gluconyl hydrazide The compounds are prepared most easily by the reaction of the appropriate alkyl hydrazine and gluconolactone in a mutual solvent, as for example, ethanol or dimethyformamide. The solid product can be purified by recrystallization from alcohol-ether or alcohol-petroleum ether or similar mixtures of solvents in a manner well-known to the art.

In applying the compounds, it can be admixed with detergents, surface active agents, emulsifiers, adjuvants, or other agents.

Liquid compositions containing the desired amount of active agent are prepared by dissolving the substance in an organic liquid or by dispersing the substance in water with or without the aid of a suitable surface active dispersing agent such as an ionic or non-ionic emulsifying agent. Such compositions can also contain modifying substances which serve as a "spreader". Suitable organic liquid carriers include the agricultural spray oils and the petroleum distillates such as diesel fuel, kerosene, fuel oil naphthas, and Stoddard solvent. Among such liquids, the petroleum distillates are generally preferred. The aqueous compositions can contain one or more water immiscible solvents for the toxicant compound. In such compositions, the carrier comprises an aqueous emulsion, e.g., a mixture of water, emulsifying agent and water immiscible solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sufonates, polyoxyalkylene derivatives or sorbitan esters, complex ether alcohols, and the like. Representative surface active agents which are suitably employed in implementing the present invention are identified in U.S. Pat. Nos. 3,095,299, second column, lines 25–36; 2,655,447, column 5; and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified in incorporation therein of an effective amount of a surfactant which facilitates the dispersion and spreading of the formulation.

EXAMPLE I

Gluconolactone, 7.2 g., is partially dissolved in 200 ml of ethanol and 20 ml of methyl hydrazine is added. The white precipitate which forms is recovered from the volatile starting materials by evaporation in vacuo. The residue is recrystallized from a 1:1 methanol-diethyl ether solution, M.P. 154°–156° C.

by the same method is prepared: Gluconyl hydrazide, M.P. 146°–148° C.

EXAMPLE II

Gluconolactone, 7.2 g., is dissolved in 200 ml of dimethyl-formamide and 35 g. of methyl hydrazine is added. An exothermic reaction is noted. The resulting hydrazide is isolated by evaporation of the solvent in vacuo and recrystallization of the residue.

By the same method is prepared:
N-ethyl gluconyl hydrazide
N-n-propyl gluconyl hydrazide
N-isopropyl gluconyl hydrazide
N-n-butyl gluconyl hydrazide
N-isobutyl gluconyl hydrazide
N-sec-butyl gluconyl hydrazide
N-tert-butyl gluconyl hydrazide Activity of the compounds has been observed by testing a 2% aqueous solution of the compound against a growing organism on an agar plate.

Further testing in aqueous systems has been accomplished by adding the compound at 0.05 to 0.2 M concentration to a contaminated aqueous system. Inhibition at 24 and 48 hours was observed in both tests. The compounds show active inhibition against the following microorganisms:

*Enterobacter cloacae*
*Escherchia coli*
*Klebsiella pneumoniae*
*Proteus vulgaris*
*Pseudomonas aeruginosa*
*Salmonella typhimurium*
*Serratia marcescens*
*Staphylococcus aureus*
*Staphylococcus epidermidis*
*Streptococcus pyogenes*
*Trichoderma viride*
*Saccharomyces cerevisiae*
*Dunaliella tertiolecta*

We claim:

1. A method of interrupting the metamorphosis of southern army worm by application to a larvae infested area a metamorphosis inhibiting effective amount of an N-(lower alkyl)gluconyl hydrazide.

* * * * *